United States Patent [19]  [11] 3,932,127
D'Albignac  [45] Jan. 13, 1976

[54] DYEING TEXTILE MATERIALS OF A BASIC CHARACTER
[75] Inventor: Jean Marie Louis Jules D'Albignac, Creil, France
[73] Assignee: Groupement d'Interet Economique Stx, Paris, France
[22] Filed: Jan. 26, 1973
[21] Appl. No.: 326,909

[30] Foreign Application Priority Data
Jan. 26, 1972  France .............................. 72.02512

[52] U.S. Cl. .............................. 8/173; 8/93; 8/174
[51] Int. Cl.² ............................................ D06P 5/04
[58] Field of Search ........................... 8/93, 173, 174

[56] References Cited
UNITED STATES PATENTS
| | | | |
|---|---|---|---|
| 3,112,983 | 12/1963 | Collins | 8/54 |
| 3,170,757 | 2/1965 | Gift et al. | 8/55 |
| 3,667,898 | 6/1972 | Bergman et al. | 8/94 |

Primary Examiner—Benjamin R. Padgett
Assistant Examiner—B. Hunt
Attorney, Agent, or Firm—Browne, Beveridge, DeGrandi & Kline

[57] ABSTRACT

Process for dyeing, by exhaustion, textile fibres of basic character with anionic dyestuffs in a solvent medium in the presence or absence of water wherein the dyebath is a homogeneous ionising liquid medium and the cations of the bath are replaced by $H^+$ protons in the course of the dyeing, the latter being effected at a temperature equal to or less than 80°C. and apparatus for use of this process which comprises apparatus for dyeing according to the process claimed in claim 1 which comprises a dyeing vessel for dyeing with solvents, a circuit for removing the dyebath continuously or by fractions, means for substituting the cations of the bath with $H^+$ protons, a recycling circuit ensuring the reintroduction into the vessel of the bath from which all or part of its cations have been removed, means for regulating the flow and means for regulating the temperature.

10 Claims, 1 Drawing Figure

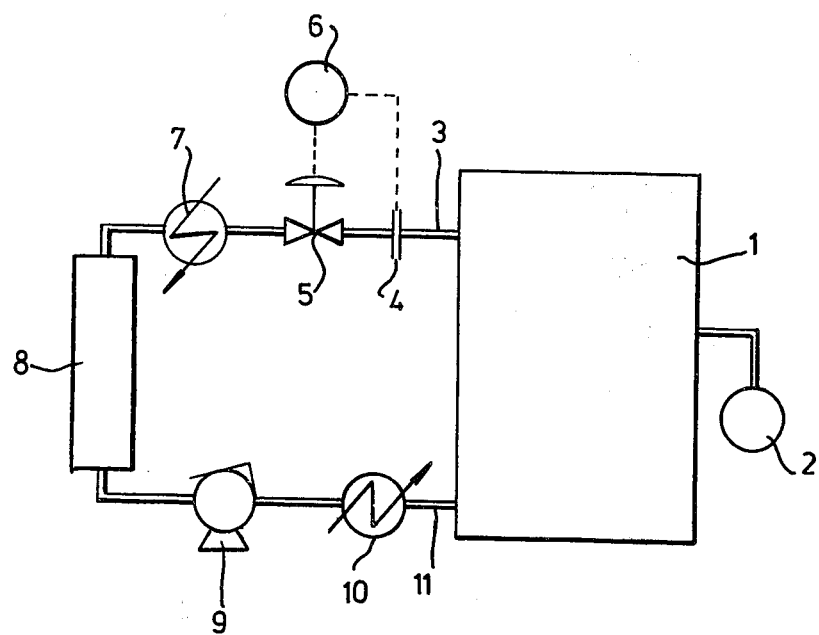

DYEING TEXTILE MATERIALS OF A BASIC CHARACTER

The invention relates to a new process for dyeing, by exhaustion, fibres and textile material of basic character with anionic dyestuffs in a solvent medium; and to apparatus for carrying out this process.

When dyeing is effected in purely aqueous baths, it is customary to add a mineral or organic acid to the dye bath in order to cause the dyestuff to be absorbed on the fibres and to encourage the exhaustion of the bath. When, on the contrary, dyeing is effected in a pure solvent medium, the addition of acid does not generally allow complete exhaustion to be obtained. On the other hand, the purification and recycling of the baths containing acid raise problems of great complexity.

An object of the invention is to provide an advantageous solution to the relative needs of the exhaustion of the baths and the regeneration of the latter.

According to the present invention a process for dyeing, by exhaustion, textile fibres of basic character with with anionic dyestuffs in a solvent medium, possibly containing water, is provided in which a dyebath is used which comprises a homogeneous ionising liquid medium, the cations of the bath being replaced by $H^+$ protons in the course of the dyeing.

A dyebath usually contains cations of very diverse origin. For example, there may be those of anionic dyestuffs of which the sulphonic or carboxylic groups have formed salts with alkali metal atoms; those of the products from mixtures, such as sodium sulphate, sodium chloride, when the dyestuff is not delivered in the pure state; and those of electrolytes which impregnate the fibres.

It has been found that on substituting protons for these cations during the dyeing operation itself that is in proportion to the absorption of the anionic dyestuff, it is possible to obtain a complete exhaustion of the dyebaths and, also to obtain exhausted baths which may be used directly for a subsequent operation.

This substitution may be effected by various means such as for example the use of cation exchange resins, dialysis, electrodialysis, electromigration. The use of resins enables the invention to be effected in a simple, convenient and effective way.

The cation exchange resins which may be used for carrying out the process of the invention may be of very diverse types for example, copolymer of styrene + sulphonated divinyl benzene, m-hydroxybenzenesulphonic acid +formaldehyde, polymethacrylate, polyacrylate, polystyrene aminodiacetate, polyalkylphosphonate or phosphate. Such resins are known on the market by the names "Amberlite", "Dowex", "Duolite", "Lewatit", "Permutite", "Wofatit", "Zeo-Karb".

The large variety of cationic resins enables one to select the resin charged with $H^+$ protons which is most suitable, having regard to the nature of the textile fibre of basic character and the constitution of the anionic dyestuff to be applied.

Thus it is that with acid dyestuffs which, in aqueous medium, need the addition of sulphuric acid in order to dye wool with complete exhaustion, a resin with sulphonate functional group charged with $H^+$ protons is preferably chosen for dyeing in a homogeneous solvent medium.

With acid dyestuffs which, for dyeing wool in aqueous medium, only need a very weak acidity, a resin with a carboxylate or aminodiacetate functional group charged with $H^+$ protons is preferably used for dyeing in a homogeneous solvent medium.

The dyebaths for the process according to the invention are generally homogeneous organic media having ionising properties. They may comprise for example polar solvents, mixtures of polar and non-polar solvents, mixtures of water and polar solvents, or ternary mixture of water, polar solvent and non-polar solvent. The proportions which it is advisable to select are those for which the constituents are miscible. Aliphatic alcohols having 1 to 7 carbon atoms may be particularly mentioned as polar solvents, while halogenated aliphatic hydrocarbons may be mentioned as nonpolar solvents. The dyeing may be effected at temperatures from ambient temperature up to 80°C.

By "anionic dyestuffs" are meant in a general way, within the compass of the invention, dyestuff having one or more acid groups in their molecule, such as sulphonic, carboxylic or phosphonic groups in the acid state or converted into a salt by an alkali metal. It is advantageous to use non-blended dyestuffs, inasmuch as the blending agents are insoluble in the solvents and, on the other hand, the saturation of the resins is effected more rapidly in their presence.

The textile fibres of basic character capable of being dyed by the new process are, for example, the natural fibres, such as wool and silk, synthetic fibres such as fibres based on polyamides, polyurethanes, basified polyalkylenes or modacrylic fibres. They may for example be in forms as diverse as flocks, slivers, threads, fabrics, knitted fabrics or non-woven materials.

The process according to the invention, with mixtures of fibres with differential dyeing affinity also enables contrast or reserve effects to be obtained which are very superior to those which are generally obtained on dyeing by exhaustion in a solvent medium.

the invention inclues apparatus enabling the dyeing to be carried out under the conditions of the present process which comprises essentially the following elements: a dyeing vessel for dyeing with solvents; a circuit for removing the dyebath continuously or in fractions; means for substituting the cations of the bath with $H^+$ protons and a recycling circuit ensuring the reintroduction into the vessel of the bath from which all or part of its cations have been removed. As accessories one may add for regulating the temperature and the flow of the bath liquid withdrawn from the vessel.

This invention will be more fully understood by reference to the drawing which is a diagram of apparatus that can be used in practicing this invention.

The attached drawing gives by way of example an installation diagram.

The dyeing vessel 1 is fitted with heating or cooling members as well as apparatus for controlling the dyebath and heat regulation 2. The choice of vessel is made having regard to the textile material to be dyed and may be for example a drum machine, paddle machine, vat or autoclave.

A system of pipes 3 for removing liquid from the dyebath is fixed on the vessel. A diaphragm for measuring the flow 4, a regulating valve 5 and a control 6 enable one to regulate the flow from the discharge pipe, and its recording. A heat exchanger 7 permits cooling of the dyebath when necessary and a suitable delivery pipe brings in the liquid at the head of the device and ensures the exchange of the cations.

When cation resin exchangers are used, the apparatus may comprise conventional columns known as "with fixed resin" or columns known as "with movable resin" which operate in countercurrent. It may also consist of interchangeable shells or cartridges which it is sufficient to replace when the resin is saturated. In a general way, it is well to provide a battery of two columns for each type of resin, of which one is in service while the other is being regenerated. The recycling circuit for the liquid leaving the exchanger 8 is constituted by a pipe 11 fitted with a pump 9 and possibly with a heater 10. Variants of the assembly shown in the drawing may be used, for example, a by-pass with a regulated flow, not fixed on the dyeing vessel but on the conventional circuit for circulating the bath, upstream or downstream of the pump, or the cation exchanger may be placed not on a by-pass or branch but directly on the circulation circuit of the bath; the whole of the bath in circulation then passes continuously over the cation exchanger. This variant is operated in particular cases such as dyeing at a temperature lower than 60°C., or dyeing with dyestuffs which, when used in an aqueous medium, require the medium to be strongly acid (pH lower than 3).

In the following Examples which are purely illustrative the parts are parts by weight unless the contrary is indicated.

EXAMPLE 1

0.3 parts of the red dyestuff consisting of the sodium salt of N-phenyl-N-ethyl-2'-sulphonamido-1-phenylazo-2-amino-8-hydroxy-naphthalene-6-sulphonic acid are dissolved in 1000 parts of methanol. This bath is introduced into an autoclave with circulation of the bath containing 40 parts of polyamide 6—6 in the form of a fibre yarn. A circuit similar to that shown in the drawing enables the bath to be passed if desired into a cylindrical column, provided with 4 parts by volume of the copolymer styrene-sulphonated divinyl-benzene, having a bridge-building rate of 8% and an exchange capacity of 4.24 milli-equivalents per gram of dry resin in the $H^+$ form. This resin is previously swollen in methanol. The height of the packing of the column is 5 times greater than its interior diameter. The bath conveyed at 55°C. is simultaneously pulsated through the textile material and the column of resin. After dyeing for 1 hour 86% of the dyestuff is fixed on the fibre.

The dyeing effected under the same conditions, but without passing the bath over the column of resin, leads to only 7% of the dyestuff being fixed on the textile material.

EXAMPLE 2

One operates under the conditions of Example 1 with a bath comprising 100 parts by volumn of methanol in which the dyestuff has previously been dissolved and 900 parts by volume of perchlorethylene. The dyeing is effected at a constant temperature of 55°C. for 30 minutes.

The bath is passed over the resin throughout the dyeing, rate of fixation of the dyestuff 98.3%. Dyeing carried out without passing over the resin leads to a rate of fixation of only 36.4%.

EXAMPLE 3

Under the conditions indicated in Example 2, 40 parts of wool which has been previously dehydrated, are dyed. On passing the bath over the resin throughout the dyeing, a rate of fixation of 62.2% is obtained. Without this passage, the of fixation is only 5.5%.

EXAMPLES 4 to 6

40 parts of wool, previously dehydrated, are dyed. The operation is effected by the process of Example 2 and 0.6 parts of the blue dyestuff consisting of the sodium salt of 2', 4', 6'-trimethyl-4-phenylamino-1-amino-anthraquinone-2-sulphonic acid are used. Dyeings for a period of half an hour are carried out at the three following temperatures: 55°C, 40°C, and 25°C. the rates of fixation (TF) of the dyestuff with and without passage of the bath over the resin are given in Table I.

Table I

|  | Temperatures | | |
|---|---|---|---|
|  | 55°C | 40°C | 25°C |
| Without passing over resin TF= | 12.2% | 3% | 1.5% |
| With passage over resin TF= | 97 % | 94% | 92.3% |

These figures show that the passage of the bath over the resin enables the temperature of dyeing to be appreciably lowered, therefore making the most of the wool, without notable reduction of the rate of exhaustion, which is not the case when the circulation of the batch over the resin is omitted. The fastness of the dyeings effected at 25°C., 40°C. and 55°C. in the presence of resin are also practically identical with one another.

EXAMPLES 7 to 10

0.6 parts of the dyestuff of Example 1 are dissolved in a bath having the following gravimetric composition:

| Methanol | 450 parts |
| Condensed water | 440 parts |
| Methylene chloride | 110 parts |

With the apparatus described in Example 1, the following are dyed for one hour at ambient temperature with and without passage over resin.

a - 40 parts of polyamide 6—6 in the form of fibre yarn
b - 40 parts of polyamide 6—6 in the form of a continuous thread
c - 40 parts of polyamide 6—6 in the form of yarn for carpet.
d - 40 parts of wool.

The rates of fixation (TF) of the dyestuff on the fibres at the end of the dyeing are indicated in Table II.

Table II

|  | Fibre yarn | Polyamide 6-6 | | Wool |
|---|---|---|---|---|
|  |  | Continuous thread | Carpet yarn |  |
| Without passage over resin TF | 50% | 9.6% | 12.9% | 3.5% |

Table II-continued

| | | Polyamide 6-6 | | |
|---|---|---|---|---|
| | Fibre yarn | Continuous thread | Carpet yarn | Wool |
| With passage over resin    TF | 97.7% | 54.5% | 63% | 78.6% |

EXAMPLE 12 the apparatus described in Example 1 is used, and the styrene-sulphonated divinylbenzene copolymer resin is replaced by the equivalent quantity of polyacrylate resin with functional carboxylate groups, having an exchange capacity of 9.5 millequivalents per gram of dry resin in the H$^+$ form. This resin is previously swollen in methanol. The dyebath consists of a mixture of 900 parts by volume of perchloroethylene and 100 parts by volume of methanol, in which 0.15 parts of the blue dyestuff constituted by the disodium salt of bis-4,4'-(4-amino-3-sulpho-antraquinonylamino)-3,3',5-,5'-tetramethyl-diphenylmethane having previously been dissolved.

The bath is passed for 15 minutes at ambient temperature over the resin, 40 parts of wool in bobbin form are introduced and the temmperature is raised to 55°C. Dyeing is effected for an hour at this temperature with continuous circulation of the bath over the resin. 92.5% of the dyestuff used is then fixed on the fibres. A dyeing test effected under identical conditions but without passage of the bath over the resin leads to a fixation of 76.2% of the dyestuff.

EXAMPLE 13

In the process of Example 12, the carboxylic resin used is replaced by the sulphonic resin of Example 1, and the bath is passed over the resin in the following manner: after 10 minutes of normal circulation of the bath, there follow 2 minutes of circulation over resin, this being carried out four consecutive times, then follows 12 minutes of normal circulation without passage over resin to finish the dyeing. A rate of fixation of 92.5% is obtained.

EXAMPLE 14

0.3 parts of the direct blue dyestuff consisting of the disodium salt of bis-3,10-(4-chloro-phenylamino)-2,9-disulpho-6,13-dichloro-triphenodioxine are dissolved in 400 parts by volume of methanol and the solution is diluted with 600 parts by volume of perchloroethylene. The batch is introduced into the autoclave apparatus of Example 1 provided with the same ion exchanger. 40 parts of polyamide 6—6 in the form of fibre thread are introduced and dyed for 15 minutes at ambient temperature, heated up to 55°C. in a period of 15 minutes and maintained for 30 minutes at this temperature, the bath passing over the resin throughout the whole of the dyeing period. The rate of fixation of the dyestuff on the fibre is 95%. the same test carried out without passage of the bath over the resin leads to a rate of fixation of the dyestuff of 66%.

EXAMPLE 15

0.1 parts of acid blue dyestuff 40 C.I. No. 62,125 are dissolved in 100 parts of methanol and the solution is then diluted with 900 parts by volume of perchloroethylene. 40 parts of material consisting of a carpet of polyamide 6—6 thread of differential affinity (deep-normal and basic dyeability) are rolled up on a cloth-beam and the bath is introduced into the circulation apparatus. During the first phase of the dyeing, a device allows the bath to pass over a column of resin having characteristics identical with those described in Example 1. When the batch is passing over the resin, the dyeing begins at 30°C. and is continued for 15 minutes at this temperature. It is then raised progressively to a temperature of 60°C. in a period of 25 minutes. At this stage the resin is short-circuited and the dyeing is continued while the temperature rises to 70°C. in 10 minutes. The dyeing vessel being then under pressure, the methanol of the bath is progressively eliminated according to the technique described in Example I of French Pat. No. 2,088,081.

Exactly the same operation is then carried out again but wihout passage of the bath over the column of resin at the start of the dyeing.

In the second case, the final exhaustion of the dyestuff is total, but while in the first case the "basic dyeable" nylon is perfectly reserved in pure white, in the second case, it is fairly strongly contaminated with blue, reducing very appreciably the contrast effect which is particularly appreciated for this kind of article.

I claim:

1. A process for dyeing, by exhaustion, textile fibres of basic character with anionic dyestuffs in an organic solvent medium wherein the dyebath is a homogeneous ionizing liquid medium and the cations of the bath are replaced by H$^+$ protons by a cation exchange resin in the course of the dyeing, the dyeing being effected at a temperature equal to or less than 80°C.

2. The process according to claim 1 wherein the textile fibres are selected from the group consisting of wool, silk, polyamides, polyurethanes, basified polyalkylenes and modacrylic fibres.

3. The process according to claim 1 wherein the homogeneous ionizing medium is selected from the group consisting of a polar solvent, a mixture of polar and non-polar solvents, a mixture of water and polar solvent and a mixture of water, polar solvent and non-polar solvent.

4. The process according to claim 1 wherein the organic solvent is an aliphatic alcohol having 1 to 7 carbon atoms.

5. The process according to claim 3 wherein the nonpolar solvent is a halogenated aliphatic hydrocarbon.

6. The process according to claim 3 wherein the homogeneous ionizing medium is a mixture of an aliphatic alcohol having 1 to 7 carbon atoms and a halogenated aliphatic hydrocarbon having 1 to 3 carbon atoms.

7. The process according to claim 6 wherein the anhydrous homogeneous ionizing medium comprises a mixture of 60% to 99% of perchloroethylene and 40% to 1% of methanol.

8. A process according to claim 6 wherein the homogeneous ionizing medium additionally contains water.

9. In a process for the dyeing, by exhaustion, of textile fibres of basic character with anionic dyestuffs in an organic solvent medium, the improvement comprises using a homogeneous ionizing liquid medium as the dyebath and the cations of the bath are replaced by H$^+$ protons by a cation exchange resin in the course of the dyeing, the dyeing being effected at a temperature equal to our less than 80°C.

10. In a process for the dyeing, by exhaustion, of textile fibres of basic character with anionic dyestuffs in an organic solvent medium, the improvement which comprises using a homogeneous ionizing liquid medium as the dyebath and contacting the dyebath with cation exchange resin to replace the cations in the dyebatch with H$^+$ protons in the course of dyeing, wherein the dyeing is effected at a temperature of equal to or less than 80°C.

* * * * *